United States Patent [19]

Ueno et al.

[11] 4,054,060
[45] Oct. 18, 1977

[54] DEVICE FOR SAMPLING FURNACE GASES

[75] Inventors: Masayuki Ueno; Fumiaki Sano, both of Yokohama, Japan

[73] Assignee: Ishikawakima-Harima Jukogyo Kabushiki Kaisha, Tokyo, Japan

[21] Appl. No.: 718,607

[22] Filed: Aug. 30, 1976

[30] Foreign Application Priority Data

Oct. 30, 1975 Japan .......................... 50-148070[U]

[51] Int. Cl.² ............................................. G01N 1/22
[52] U.S. Cl. ............................................. 73/421.5 A
[58] Field of Search .................... 73/421.5 R, 421.5 A

[56] References Cited

U.S. PATENT DOCUMENTS 3,643,508  2/1972  Schneider ...................... 73/421.5 A

*Primary Examiner*—S. Clement Swisher
*Attorney, Agent, or Firm*—Scrivener, Parker, Scrivener & Clarke

[57] ABSTRACT

The present invention discloses a furnace gas sampling device provided with a gate valve of the type in which a swingable valve disk is actuated to seal a lance insertion hole formed through the furnace wall when a lance is retracted away from the furnace and a mechanism for discharging dust and the like out of the valve box while the valve disk sealing the lance insertion hole.

4 Claims, 16 Drawing Figures

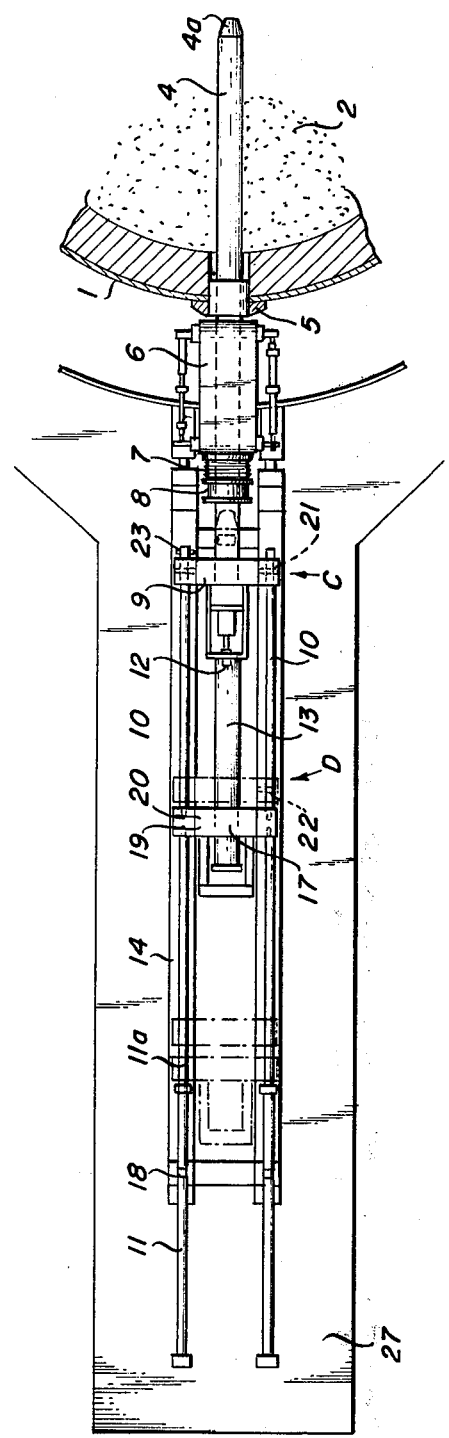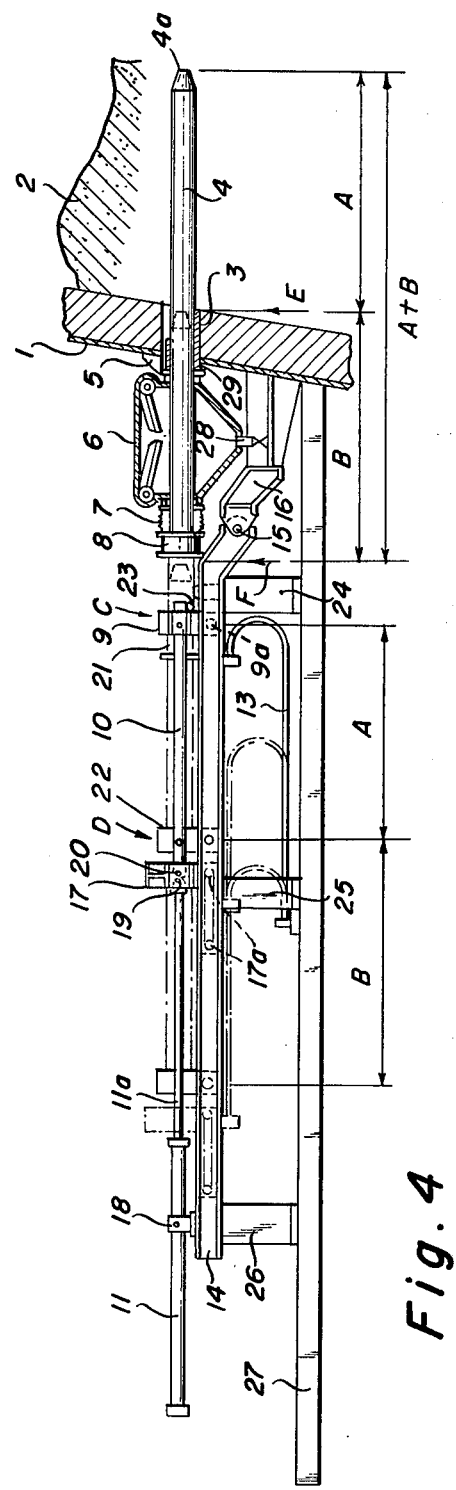

DEVICE FOR SAMPLING FURNACE GASES

BACKGROUND OF THE INVENTION

1. Field of the Invention

The present invention relates to a device for sampling gases from a furnace.

2. Description of the Prior Art

With the recent trend toward the increase in capacity of blast and vertical furnaces and the use of higher pressure, techniques must be established for operating a blast or vertical furnace at its highest efficiency in a reliable and dependable manner so that savings in expensive imported raw materials may be attained. For this purpose there has long been the demand for a device for sampling gases from a blast or vertical furnace which device is essential for the furnace operation and is highly reliable in operation and inexpensive to fabricate and install.

in FIGS. 1 and 2, there is shown one example of the prior art furnace gas sampling devices. A lance $c$ is inserted into a furnace body $a$ charged with raw materials $b$, and is extended through a gate valve $d$ and a sealing device $e$ to be connected to the piston rods of lance driving cylinders $f$ mounted on guide frames $g$ with brackets $h$.

In operation, the lance 4 whose inner end is terminated into a sampling hole or port is traversed across the furnace body $a$ over a distance substantially equal to the radius of the furnace for sampling furnace gases at several predetermined sampling points. After sampling, the inner end of the lance $c$ is retracted over a stroke A and normally held in a lance insertion hole in the furnace wall as shown by the broken lines in FIG. 2. With the lance $c$ in the retracted position, the gate valve $d$ is completely closed, and the sealing device $e$ prevents the leakage of furnace gases.

In case of failure or inspection of the lance $c$, the latter is further retracted from the normal position over a stroke B. In this case, when the inner end of the lance $c$ is located between the gate valve $d$ and the sealing device $e$, the gate valve $d$ is closed to prevent the leakage of the furnace gases.

The lance $c$ is driven by the cylinders $f$ with a relatively long stroke in excess of the whole stroke (A + B) of the lance $c$. When the capacity of a furnace is of the order of more than 4,000 m³, there must be provided hydraulic cylinders with a stroke in excess of 10 meters so that many problems arise as will be described below. Firstly, there is a buckling problem of a cylinder rod with the increase in stroke so that the cylinder rod must be increased in diameter. Then a long cylinder with a large diameter is required, but it is very difficult to fabricate such a cylinder and special materials must be selected with the resultant increase in cost. In addition, the longer the piston rod, the greater the deflection becomes.

Furthermore oil leakage tends to occur from piston rod packings because of the rupture of oil films on the piston rod surface and the adhesion of dust to the surface of the piston rod. With the increase in length of the piston rod and the cylinder, the guide frames $g$ and a deck structure for supporting the guide frames $g$ must be increased in size accordingly so that the furnace gas sampling device becomes large in size and heavy in weight and consequently the installation cost and space are increased.

The lance $c$ and the guide frames $g$ must satisfactorily follow the thermal expansion of the furnace body $a$. However since the lance $c$, the guide frames $g$ and the driving cylinders $f$ are considerably long, it is extremely difficult to fabricate and install the furnace gas sampling device with a higher degree of accuracy so that there is a danger that excess loads are exerted to the driving cylinders $f$ due to the thermal expansion of the furnace body $a$.

In the prior art furnace gas sampling devices, the gate valve $d$ is, in general, of the slide type so that a sliding plate valve tends to bite a packing too much, causing the sealing failure; that is, the leakage of high pressure furnace gases into the surrounding atmosphere.

In general, the sealing device $e$ is of the formed gland packing seal type. In this type, the whole gland packings must be replaced in case of repair so that skilled labors are required and the replacement is very tedious. Furthermore the clearance between the lance $c$ and the lance sealing members of the sealing device $e$ is very severe. If the clearance should be increased due to the abrasion, wear and thermal deformations, the leakage of furnace gases cannot be prevented.

The pin-hinged or cymbul type couplings $i$ have long been used because they may absorb the angular displacements due to the axial thrusts or axial tensile, compressive and repeated forces, but excessive axial thrusts are exerted to the coupling, resulting in the frequent breakdowns of the coupling. Furthermore the coupling is subjected to the angular displacements in all directions due to the high temperatures so that the breakdowns of the coupling tend to occur very often. The coupling $i$ must be installed with a higher degree of accuracy in all directions except a predetermined angle through which the angular displacement of the coupling is permitted so that the safety of the coupling against an unexpected factor such as the displacement in an unexpected direction due to the thermal expansion of the furnace body $a$ cannot be ensured.

SUMMARY OF THE INVENTION

In view of the above, one of the objects of the present invention is to provide a furnace gas sampling device which may substantially overcome the above and other problems encountered in the prior art devices and which is highly reliable and dependable in operation and inexpensive to manufacture, thereby ensuring the stable and highly efficient furnace operations.

The present invention will become apparent from the following description of some preferred embodiments thereof taken in conjunction with the accompanying drawings, in which:

BRIEF DESCRIPTION OF THE DRAWINGS

FIG. 3 is a top view of a furnace gas sampling device in accord with the present invention;

FIG. 4 is a side view thereof;

Same reference numerals are used to designate similar parts in FIGS. 3 through 16.

DETAILED DESCRIPTION OF THE INVENTION

General Description, FIGS. 3 and 4

Figure 1:
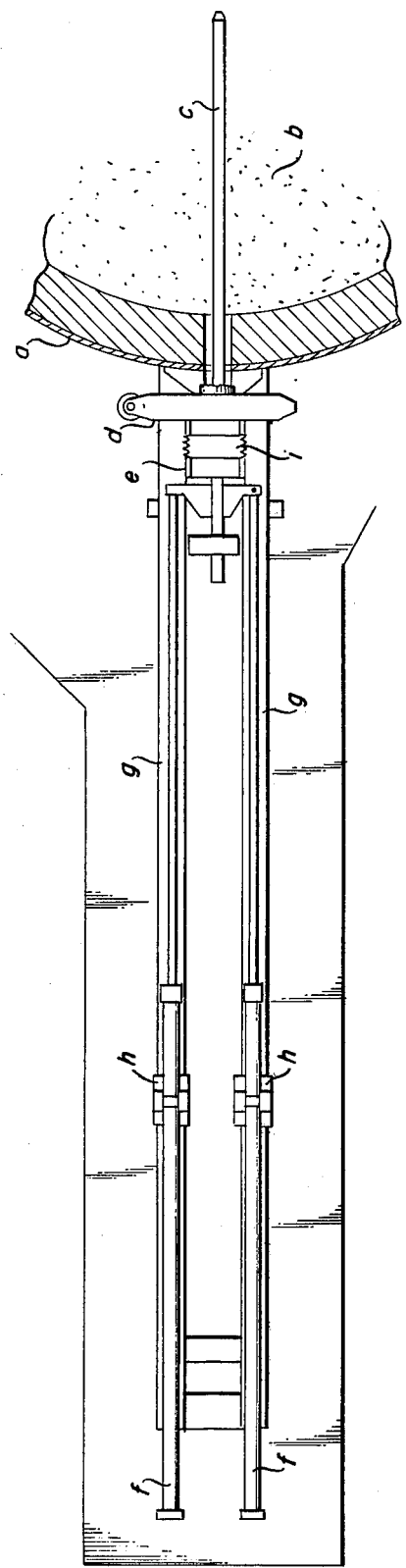
FIG. 1 is a top view of a prior art furnace gas sampling device.

A lance 4 is insertable into a furnace body 1 charged with raw materials 2 in the radial direction of the furnace body 1 through a bush fitted into a front casing 29 which in turn is fitted into a lance insertion hole formed through the furnace wall adjacent to a furnace nozzle 5. The lance 4 is extended outwardly through the casing 29, a gate valve 6, a rear casing 30, an expansion coupling 7 with a bellows and a sealing device 8 joined to each other with bolts in the order named.

The inner end of the lance 4 is terminated into a furnace gas sampling port 4a adapted to be opened or closed by a cylinder 12 (See FIG. 3), and the junction of a thermocouple is positioned adjacent the sampling port 4a. Extended through the water-cooled lance 4 are lead wires of the thermocouple and a limit switch for sensing the opening or closing of the sampling port 14a, a rubber hose for drawing sampled furnace gases as well as for purging nitrogen gas, a hose for circulating cooling water, a hose for transmitting the hydraulic pressure to closure means to open or close the sampling port 14a and the like. These wires and hoses extended out of the lance 4 from the outer end thereof are flexibly supported on a cable bearer 13 to follow the movement of the lance 4 and are connected to respective equipment, sources and the like mounted on a deck 27.

A pair of parallel guide frames 14 having an H-shaped cross sectional configuration are supported on the deck 27 by front, intermediate and rear supports 24, 25 and 26, and the front ends of the guide frames 14 are connected to a frame 16 mounted on the furnace body 1 with pins 15 inserted into elongated slots formed in the frame 16.

Alternatively, the guide frames 14 may be supported by the pins 15 inserted into round holes formed through the frame 16 and the rear supports 26 which are of the linkage type so that the frame guides 14 may be shortened in length and may more easily follow the thermal expansion of the furnace body 1 as will be described in detail hereinafter.

The rear end of the lance 4 is supported on a lance supporting bracket 9 which has wheels 9a riding on the inner flanges of the H-shaped frames 14 so that the lance supporting bracket 9 is movable along the guide frames 14.

A wheeled carriage 17 with four single-flange wheels 17a are mounted on the guide frames 14 rearwardly of the movable bracket 9 for movement along the guide frames 14.

A lance driving cylinder 11 is pivoted with a trunnion to a bracket 18 which in turn is securely mounted on the guide frame 14 at the rear end thereof, so that the cylinder 11 may swing in a vertical plane.

The leading end of the piston rod 11a of each hydraulic power cylinders 11 is connected with a pin 19 to the carriage 17. The rear ends of a pair of parallel links 10 are connected with pins 20 to the carriage 17 while the front ends of the links 10 are normally connected with pins 21 to the movable bracket 9 and are supported by link supporting rollers 23 riding on the guide frames 14. An emergency connection pin hole 22 is formed through each link 10 adjacent to the rear end thereof and spaced apart from the pin 21 by a distance equal to a sampling stroke A of the lance 4 for the purpose to be described hereinafter.

The axes of the driving cylinders 11 and piston rods 11a, the links 10 and the lance 4 are in the same horizontal plane and are parallel to each other. Upon actuation of the power cylinders 11, the piston rods 11a are extended or retracted so that the lance 4, which are drivingly coupled through the movable bracket 9, the links 10 and the carriage 17 to the piston rods 11a, may be advanced into or retracted from the furnace.

Except for the sampling operation in which the lance 4 is advanced over the sampling stroke A into the furnace, the inner end of the lance 4 is normally held in the bush 3 or in the retracted position E, and the gate valve 6 is wide opened so that the pressure in the gate valve 6 and the expansion coupling 7 is same with the pressure in the furnace. Dust discharge valves 28 at the bottom of the gate valve 6 are closed, and the rear end of the bellows of the expansion coupling 6 is closed by the sealing device 8 to be described in detail hereinafter.

In case of inspection, repair or emergency, the inner end of the lance 4 must be further retracted a stroke B from the normal retracted position E to the emergency position F, and while the inner end portion of the lance 4 is still in sealing engagement with the sealing device 8 the gate valve 6 is closed to seal the furnace gases. For this purpose the stroke of the piston rod of each cylinder 11 is selected equal to the longer stroke of either the stroke A or B. (The stroke A is, in general, longer than the stroke B in the recently constructed furnaces with a large capacity.) When the inner end of the lance 4 is retracted to the normal retracted position E, the connecting pins 21 for interconnecting between the movable bracket 9 and the front ends of the links 10 are located in alignment with the emergency holes 22 or emergency connection position D spaced apart by the distance A from the position C where the pins 21 are located when the inner end of the lance 4 is in the normal retracted position E. Under these conditions the piston rods 11a of the hydraulic cylinders 11 are completely retracted. Then the connecting pins 21 are pulled out, and piston rods 11a are extended again over the distance or stroke A so that the pin holes of the movable bracket 9 may be aligned with the emergency holes 22. Therefore the connecting pins may be inserted into these aligned holes to interconnect between the movable carriage 9 and the links 10. Thereafter the piston rods 11a are retracted again over the stroke B so that the inner end of the lance 4 is pulled out of the sealing device 8 and retracted to and held in the emergency position F.

To return the lance to the normal or operative position, the above steps are reversed. More particularly, the piston rods 11a are extended to advance the inner end of the lance to the normal retracted position E, and then the connecting pins are pulled out of the holes of the movable bracket 9 and the emergency connection holes 22. Thereafter piston rods 11a are retracted over the stroke A so that the normal connection holes adjacent the front ends of the links 10 are aligned with the pin holes of the movable bracket 9 remaining at the emergency position D. The connecting pins 21 are inserted into the aligned pin holes to interconnect between the bracket 9 and the links 10 in the normal manner.

In the above link connection changeover steps, the link supporting rollers 23 ensure the smooth movement over the guide frames 14 of the links 10 disconnected from the movable bracket 9.

Figure 2:
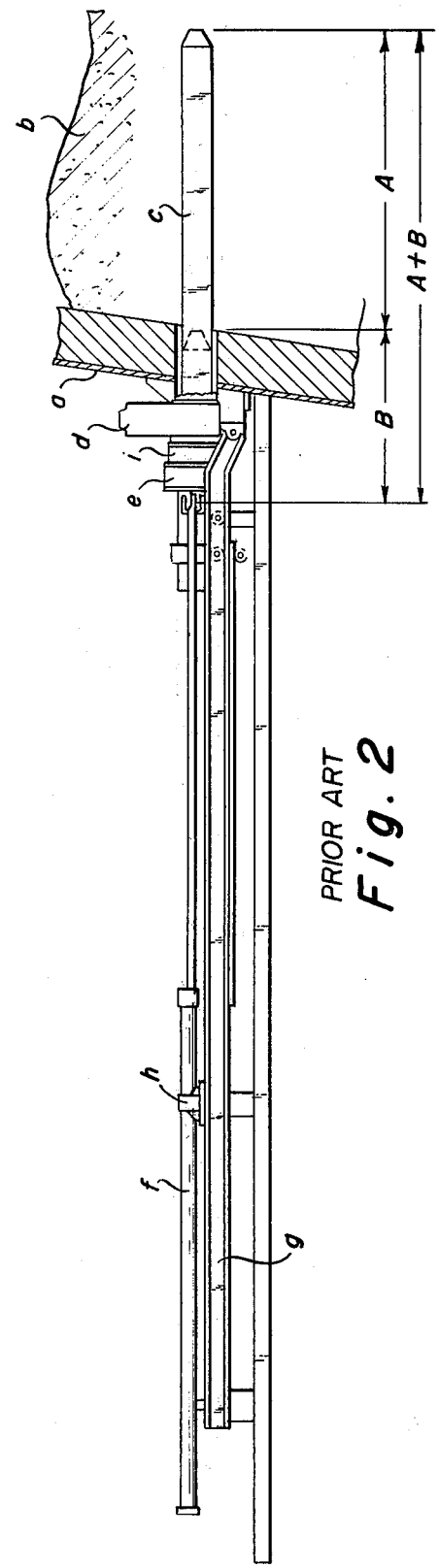
FIG. 2 is a side view thereof.

According to the present invention the buckling problem of the piston rods may be substantially overcome. Whereas in the prior art furnace gas sampling device shown in FIGS. 1 and 2 the length of the piston rod subjected to the buckling is from the bracket h to the leading end of the piston rod connected directly to the rear end of the lance, in the device in accord with the present invention, the length of the piston rod subjected to buckling is from the bracket 18 to the leading end of the piston rod connected the wheeled carriage 17. In other words, the length of the piston rod 11a is almost one half of the length of the piston rod of the prior art device. That is, whereas the long piston rod is directly connected to the rear end of the lance in the prior art device, the piston rods are connected through the links 10 to the rear end of the lance 4 in the device in accord with the present invention. As a result, the fabrication of the hydraulic cylinders may be much facilitated and the cost is reduced accordingly.

Furthermore since the connecting pins are used in the connection between the piston rods 11a and the wheeled carriage 17, between the links 10 and the wheeled carriage 17 and the movable bracket 9 and between the lance 4 and the movable bracket 9, the piston rods 11a, the links 10 and the lance 4 may easily follow the thermal expansion of the furnace body 1.

Moreover the guide frames for supporting the driving cylinders 11 and the deck 27 are reduced in length, the installation space and cost can be reduced. Since the length of the hydraulic cylinders 11 are about one half of that of the cylinders used in the prior art device, the deflection of the piston rods is less, and the rupture of oil films on the piston rods and the adhesion of dust or the like to them are minimized so that the leakage from the rod packings may be minimized.

The driving cylinders 11 are held stationary so that a cable bearer for flexibly supporting the hydraulic pressure transmission lines to the cylinders 11 may be eliminated and the hydraulic circuitry may be simplified accordingly. Furthermore the hydraulic cylinder connection is simple so that the installation cost may be reduced.

Figure 5:
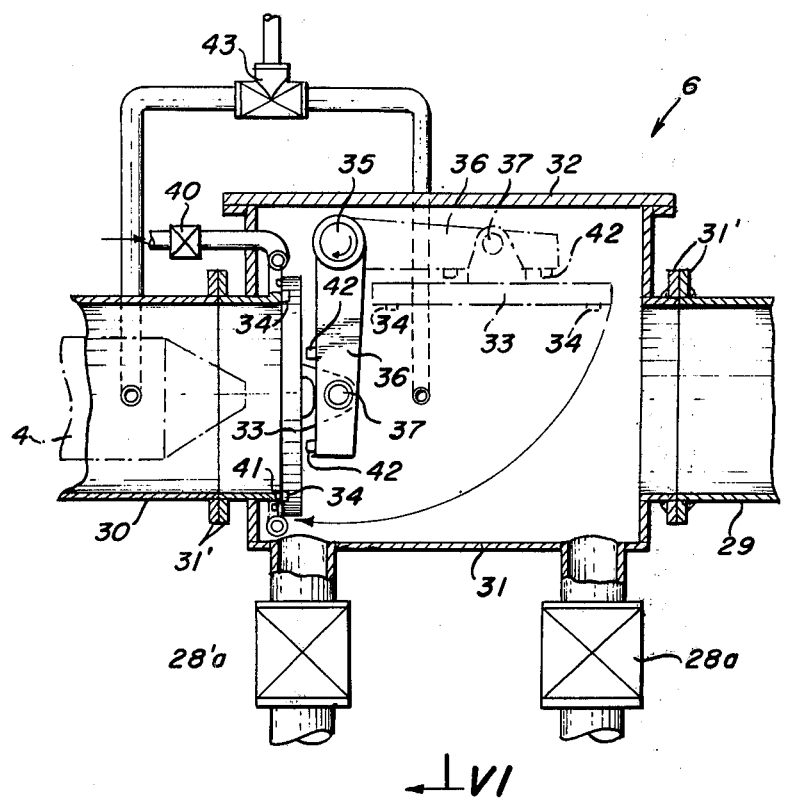
FIG. 5 is a sectional view of a first embodiment of a gate valve used in the furnace gas sampling device shown in FIGS. 3 and 4.
Figure 6:
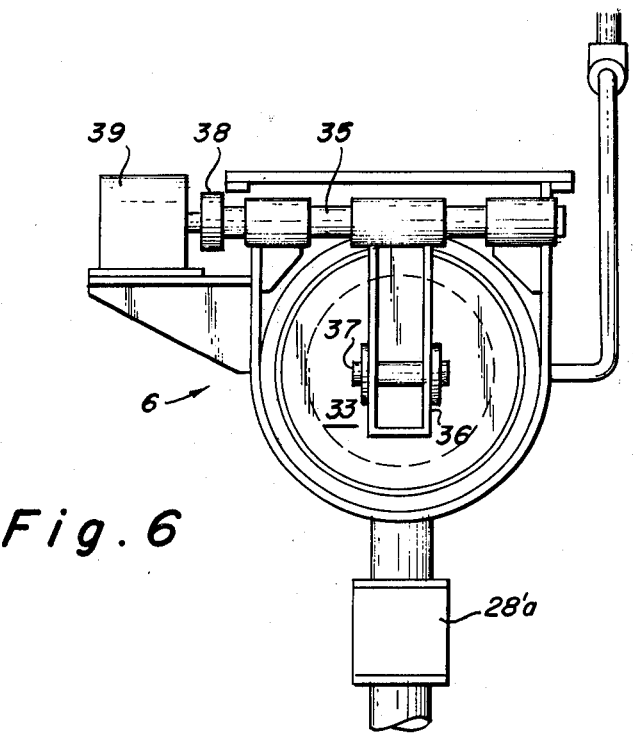
FIG. 6 is a sectional view taken along the line VI — VI of FIG. 5.
Figure 7:
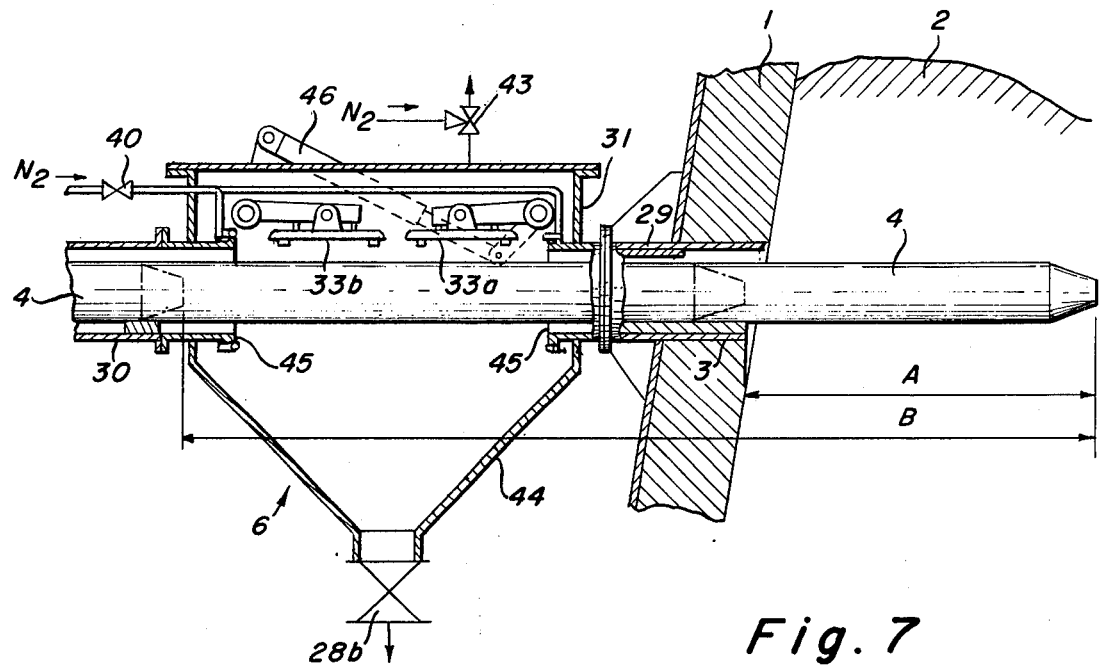
FIG. 7 is a sectional view of a second embodiment of a gate valve in accord with the present invention.

Gate Valve, FIGS. 5, 6 and 7

In FIGS. 5 and 6 there is shown a first embodiment of a gate valve 6 used in the present invention. A valve box 31 with a top 32 is constructed to resist high pressures and has its flanges 31' joined to the flanges of the casings 29 and 30. A valve disk 33 mounted with heat resisting packings 34 is pivoted with a pin 37 to a supporting arm 36 which in turn is carried by a driving shaft 35 connected through a shaft coupling 38 to an actuator 39 such as an electric motor or oil motor. Alternatively, a combination of a hydraulic power cylinder and a linkage may be used to shift the valve disk 33.

Next the mode of operation for retracting the inner end of the lance 4 to the position indicated by the broken lines in FIG. 5 will be described. First the actuator 39 is energized to bring the valve disk 33 or packings 34 to the almost closed position, and then a dust purging gas cock 40 is opened to introduce the purging gas such as $N_2$ so as to remove dust or the like attached to the sealing surfaces of the packings 34 and a valve seat 41. Thereafter the actuator 39 is energized to drive the valve disk 33 to press the packings 34 against the valve seat 41, thereby completely closing the opening of the casing 30 as indicated by the solid lines in FIG. 5. While gas purging is still continued. The stoppers 42 attached to the supporting arm 36 serve to limit the angle of rotation of the valve disk 33 about the pivot pin 37. Next a three-way valve 43 connected to the pipe line interconnecting between the casing 31 and the valve box 31 is changed over so that the casing 31 is communicated through the three-way valve with the surrounding atmosphere.

To open the gate valve 6, the three-way valve 43 is so actuated as to admit $N_2$ gas or the like, thereby reducing the pressure difference across the valve disk 33 to zero, and then the actuator 39 is energized to shift the valve disk 33 away from the valve seat 41.

To remove the dust in the valve box 31, the dust discharge valves 28a and 28a' are opened. However it will be understood that any suitable dust removal means may be used.

In FIG. 7 there is shown a second embodiment of the gate valve in accord with the present invention. Within the valve box 31 of the gate valve 6 there are disposed front and rear valve disks 33a and 33b for closing the openings of the front and rear casings 29 and 30, respectively, when the lance 4 is retracted out of the gate valve 6. When the lance 4 is advanced into the furnace as indicated by the solid lines in FIG. 7, the front and rear valve disks 33a and 33b are retracted and held in the inoperative position indicated by the solid lines so that the pressure in the front and rear casings 29 and 30 and the valve box 31 is same with the pressure in the furnace. In this case, the opening at the bottom of a hopper 44 connected to the valve box 31 is closed by a dust discharge mechanism which is shown as a valve in this embodiment, but any other suitable means may be used. The casing 30 is sealed by the sealing device to be described in detail hereinafter.

Dust suspended in the valve box 31 as well as particles of iron ores and coke entrained by the lance 4 are gradually accumulated on the bottom of the hopper 44. To discharge these accumulated dust and particles from the hopper 44, the lance 4 is retracted so that its inner end is located in the rear casing 30 as indicated by the broken lines. Thereafter the dust purging gas cock 40 is opened to admit the purging gas such as $N_2$ into the valve box 31 to blast off dust or the like attached to the vicinity of the openings 45 of the front and rear casings 29 and 30. Next the actuator or hydraulic cylinder 46 is energized to drive the front and rear valve disks 33a and 33b to press them against the openings 45 so that the valve box 31 is sealed from the front and rear casings 29 and 30. Thereafter the three-way valve 43 is changed over to discharge the gases in the box 31 into the surrounding atmosphere, and then the dust discharge mechanism 28b is opened to discharge dust or the like.

Only the front disk 33a may be actuated to close the front opening 45 when dust or the like is to be discharged. In this case, the gases in the valve box 31 and the rear casing 30 are discharged through the three-way valve 43 before the dust discharge mechanism 28b is opened.

After dust or the like is discharged, the dust discharge mechanism 28b is closed and the three-way valve 43 is so actuated as to admit high pressure gas such as $N_2$ into the valve box 31 until the pressure in the latter becomes equal to the pressure in the furnace. Thereafter the front and rear valve disks 33a and 33b are moved away from the front and rear openings 45 to permit the advance of the lance 4 to the normal retracted position or into the furnace. It is preferable to use $N_2$ gas as a high pressure gas admitted through the three-way valve 43 into the valve box 31, but it will be understood that any other suitable gas may be required as needs demand.

According to the present invention, the sampling opening 4a and the conditions of the lance 4 may be inspected in the manner described above. This is possible even when the furnace is operating because the gate valve 6 has the front valve disk 33a to seal the front opening 45 so that the inspection or modification of the lance 4 may be continued for a relatively long time. Even though it is not shown, an inspection hole or the like is provided for the top 32 of the valve box 31.

In addition to the advantage that the gate valve 6 may be used in either the single-point or multi-point measurement mode, the gate valve 6 in accordance with the present invention has the following advantages;

I. Since the valve disks with the ability of attaining the excellent sealing effect are pressed against the front and rear casings, the sealing effect is considerably improved over the prior art gate valves, Since the sealing surfaces are not provided with sliding parts, lubrication may be eliminated.

II. Dust (including particles of ores and coke) accumulated in the valve box may be completely discharged.

III. Inspection, repair and modification of the device may be made any time; that is, not only during the time when the furnace operation is interrupted but also during the operation of the furnace.

IV. The interruption of the furnace operation due to the breakdowns of the furnace gas sampling device may be eliminated.

V. Since no lubrication is required, moving parts remain dried, and the inert purging gas such as $N_2$ is blasted so that the adhesion of dust or the like to moving parts may be eliminated and consequently the highly effective sealing effect can be attained.

Sealing Device, FIGS. 8 through 12

Next some preferred embodiment of the sealing device in accord with the present invention will be described with reference to FIGS. 8 through 12.

Figure 8:
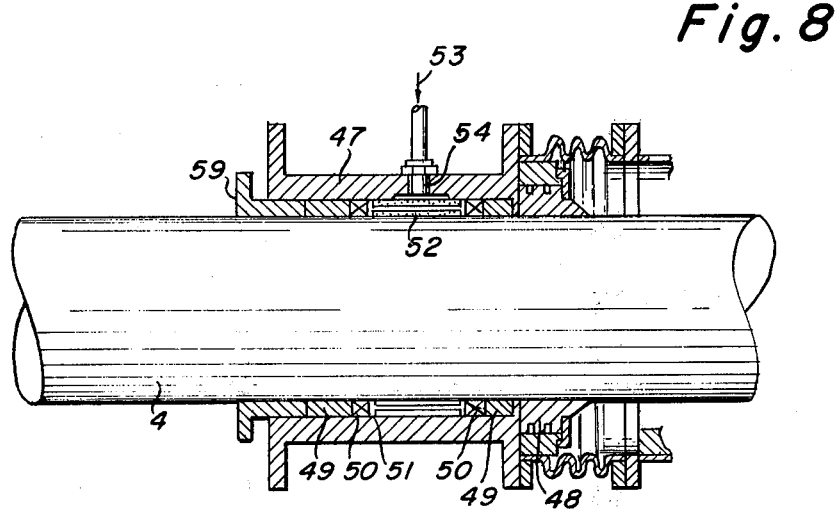
FIG. 8 is a sectional view of a first embodiment of a sealing device in accord with the present invention.

In FIG. 8, there is shown a first embodiment of the type defining only one sealing section between the lance 4 and a housing 47 which is straight. The sealing device comprises the housing 47, a scraper 48 located at the front end of the housing, a pair of axially spaced oilless metals 49, a pair of formed gland packings 50 located adjacent to the inner sides of the oilless metals 49, a lantern ring 51 and a packing retainer 59, the oilless metals 49, the gland packings 50 and the lantern ring 51 being placed in the sealing section defined between the lance 4 and the inner wall surface of the housing 47. The housing 47 is provided with an inlet or charging port 54 for forcing amorphous heat-resisting sealing material 53 into the space 52 defined between the pair of axially spaced formed gland packings 50.

Figure 11:
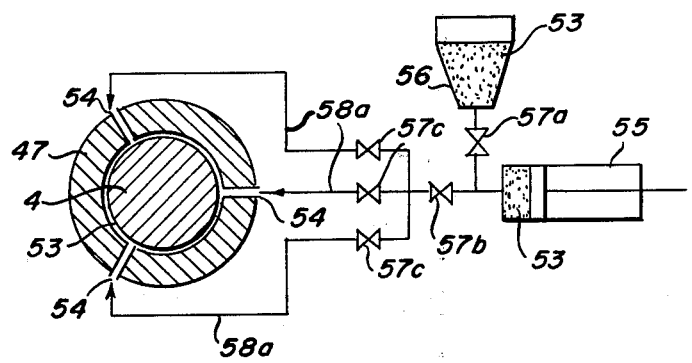
FIG. 11 is a view used for the explanation of a first embodiment of a sealing material supply or feed system in accord with the present invention used for feeding the sealing material to the sealing devices shown in FIGS. 8 and 9.
Figure 12:
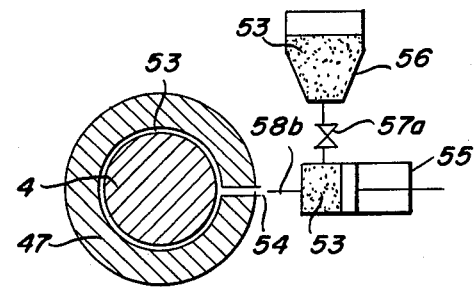
FIG. 12 is a view used for the explanation of a second embodiment of a sealing material supply or feed system.

The system for charging amorphous heat-resisting packing material under pressure into the space 52 consists of, as shown in FIG. 11 or 12, a hydraulically-operated pressure cylinder or spreader 55, a sealing material supply device 56 such as a hopper which may be manually, electrically or hydraulically driven, stop valves 57a, 57b and 57c and feed lines 58a and 58b.

Amorphous sealing material 53 is selected from the materials capable of resisting high temperatures and attaining high sealing effects. It may be prepared by mixing, for instance, finely divided particles of fluorine tetrachlorine, amphibole asbestos, an adhessive, heat-resisting lubricant and the like so that the mixture may have suitable plascity (flowbility).

Next the mode of operation of the sealing device will be described. The amorphous heat-resisting sealing charge is supplied into the supply device 56, and then the stop valve 57a is opened to admit the sealing charge 53 into the cylinder 55 while the stop valve 57b is kept closed. After the sealing material 53 is charged into the cylinder 55, the stop valve 57a is closed and the stop valves 57b and 57c are opened and the pressure cylinder 55 is actuated so that the pressurized sealing charge 53 may be forced through the charging port 54 into the space 52 between the packings 50.

In the first embodiment shown in FIG. 11, the sealing charge may be forced into the space 52 through three ports 54, and the charged sealing material may be maintained at a predetermined pressure by the pressure cylinder 55 so that the pressure in the furnace of the order of 3 $Kg/cm^2$ may be completely sealed even when the lance 4 is advanced forwardly or backwardly through the sealing device.

In a second embodiment of the sealing device shown in FIG. 12, the sealing material supply device 56 is directly communicated through the stop valve 57a to the pressure cylinder 55, and only one sealing charge inlet port 54 is provided. The mode of operation is substantially similar to that of the first embodiment described above.

When a plurality of sealing material charging ports are provided, the sealing charge 53 may be immediately uniformly distributed around the lance 4 so that the lubrication and sealing effects may be remarkably improved.

As to the method for pressurizing the sealing material to be charged into the sealing device, the sealing charge supply device may be communicated with the pressure cylinder 55 in either method shown in FIG. 11 or 12.

The high sealing effects of the sealing device with the above construction were confirmed by the experiments conducted by the inventors. That is, when the furnace pressure of the order of 3 $Kg/cm^2$ G was leaking through the clearance between the packing retainer 59 and the lance 4, the sealing charge 53 was forced into the space 52 for a few seconds. Then the leakage was completly prevented. Even when the lance 4 was shifted 7 to 8 times over a stroke of 1000 mm after only one charging of the sealing material, the satisfactory lubrication as well as sealing were maintained. As is clear from the above experimental data, the sealing device in accord with the present invention can attain the complete sealing and lubrication under high pressures by charging the amorphous heat-resisting sealing material 53 under pressure into the space 52 and maintaining the pressure of the sealing material charged into the space 52.

Figure 9:
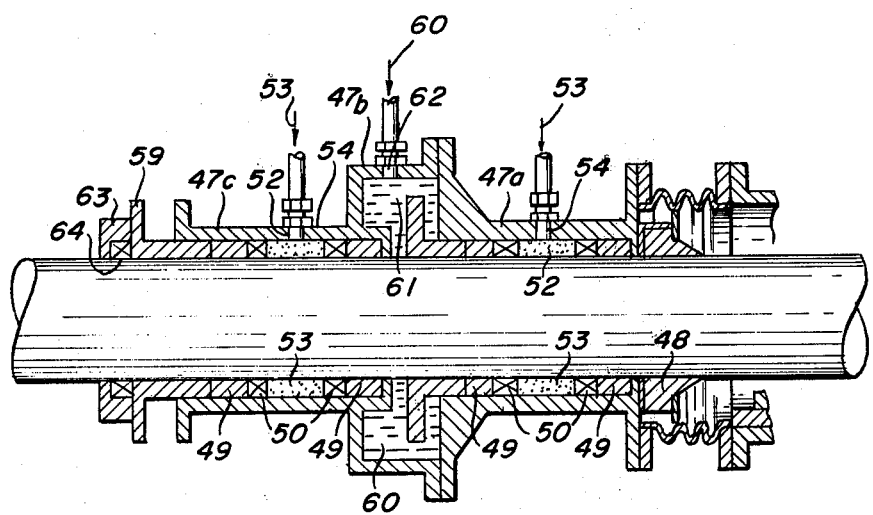
FIG. 9 is a sectional view of a second embodiment of a sealing device in accord with the present invention.
Figure 10:
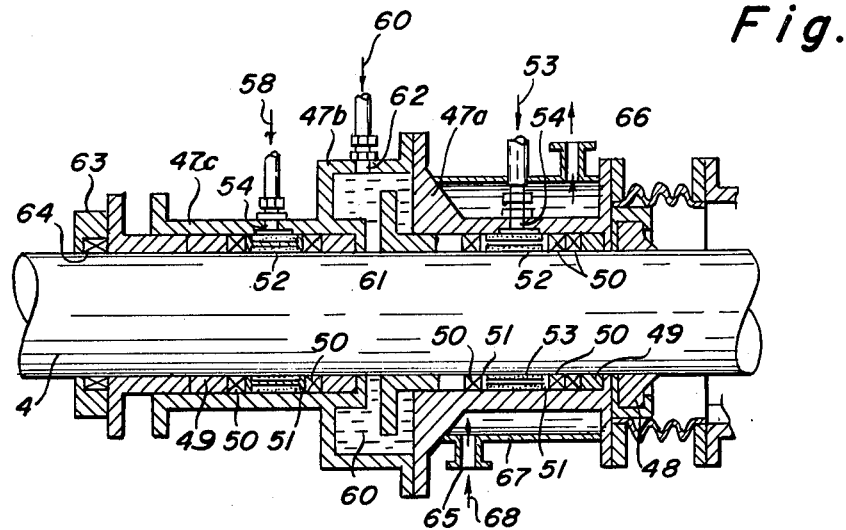
FIG. 10 is a sectional view of a third embodiment of a sealing device in accord with the present invention.

In a second and third embodiments shown in FIGS. 9 and 10, there are provided three sealing sections between the lance 4 and three housing sections 47a, 47b and 47c.

In the second embodiment shown in FIG. 9, a pair of axially spaced oilless metals 49 and a pair of axially spaced formed gland packings 50 are interposed between the housing 47a or 47c and the lance in each of the first and second sealing sections, and the packing retainer 59 is fitted into the third housing section 57c. As with the case of the first embodiment described with reference to FIG. 8, the amorphous heat-resisting sealing charge 53 is forced into the space 52 defined between the pair of gland packings 50 and is maintained at a predetermined pressure to seal to furnace pressure.

In the second sealing section or even-numbered housing section 47b, a lubricant 60 is charged through an inlet port 62 into a chamber or space 61 defined within the housing section 47b. A dust keeper housing 63 with a dust keeper 64 is attached to the packing retainer 59.

In the third embodiment shown in FIG. 10, in order to attain more effective sealing effects and encounter the high temperatures (the temperature in the furnace being 900° C in case of an accident), the lantern ring 51 is interposed between the formed gland packings 50 in the first and second sealing sections or housing sections 47a and 47c. In addition to the cooling system for cooling the inner surface of the lance 4, there is provided a water jacket or casing 67 surrouding the first housing section 47a on the side of the furnace and having a water inlet port 65 and a water discharge port 66 for circulating cooling water 68. In order to encounter high temperatures or to prevent the intrusion of dust, it is preferable to interpose a plurality of formed gland packings 50 (two being shown in this embodiment) at the inner end of the first sealing or housing section 47a.

Figure 13:
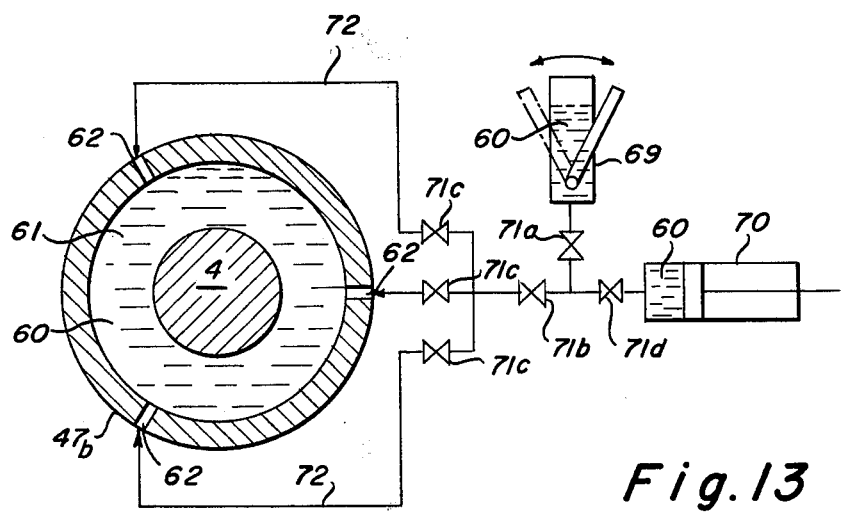
FIG. 13 is a view used for the explanation of a third embodiment of a sealing material feed system.

The charging of the amorphous heat-resisting material 53 is made in the manner described above with reference to FIGS. 9 and 10. A system for charging the lubricant 60 into the second sealing or housing section 47b is shown in FIG. 13, and consists of lubricant supply device or feeder 69, a pressure cylinder 70, stop valves 71a, 71b, 71c and 71d and a feed line 72. The mode of operation of this lubricant supply system is substantially similar to that of the sealing material charging systems described above. In the lubricant supply system shown in FIG. 13, the lubricant is charged into the space 61 through three ports 62, but only one port 62 may be provided. It is preferable to use a heat-resisting grease as a lubricant.

In the second and third embodiments described above with the reference to FIGS. 9 and 10, the combination of the sealing material charging system with the lubricant charging system can attain the perfect lubrication and sealing under the severe working conditions as with the case of the first embodiment.

The advantages of the sealing devices in accord with the present invention may be summarized as follows:

I. Sealing effects can be remarkably improved. Since the amorphous heat-resisting material is charged and maintained at a high pressure level, it may effectively seal the lance 4 even when it has some surface defects such as damages and wear or it is deformed under the influence of heat or it has some dimmensional errors. Therefore the sealing devices in accord with the present invention can attain the satisfactory sealing even such severe conditions that the prior art sealing devices fail to seal.

II. Satisfactory lubrication of the lance 4 may be attained because of the high lubrication ability of the amorphous heat-resisting material.

III. The safeguarded operations of and around the furnace gas sampling device may be ensured, and the reliability of the furnace gas sampling device may be considerably improved.

IV. Easy maintenance and savings in labor may be attained. In the prior art formed gland packing sealing systems, whenever gases leak, the packing retainers or the like must be tightened further, and the sealing device must be disassembled in order to replace the aged worn or damaged gland packings. Therefore a considerably long time and skilled labors are required for maintenance. In accordance with the present invention however the replacement of gland packings may be almost eliminated because the amorphous heat-resisting material may be intermittently charged into the sealing device so that considerable savings in maintenance cost and labor can be attained.

V. Since the sealing material charging system may electromagnetically or hydraulically remote controlled, it may be automated so that further savings in labor can be attained.

Figure 14:
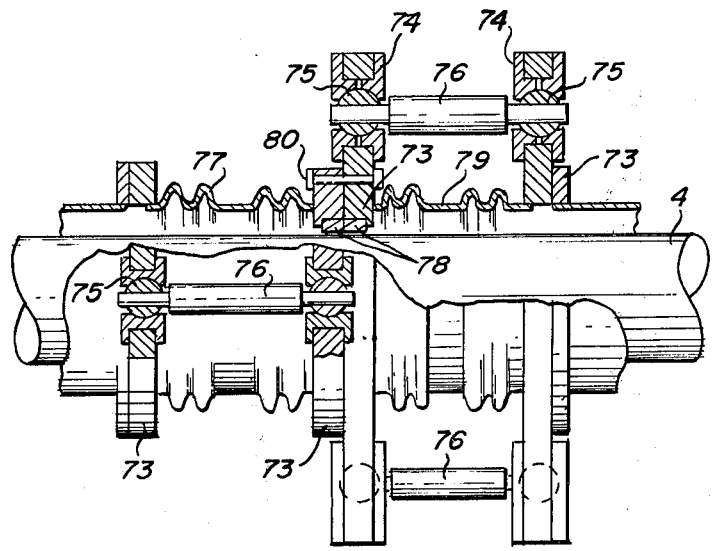
FIG. 14 is side view with parts broken of a first embodiment of a coupling device used in the present invention.
Figures 15, 16:
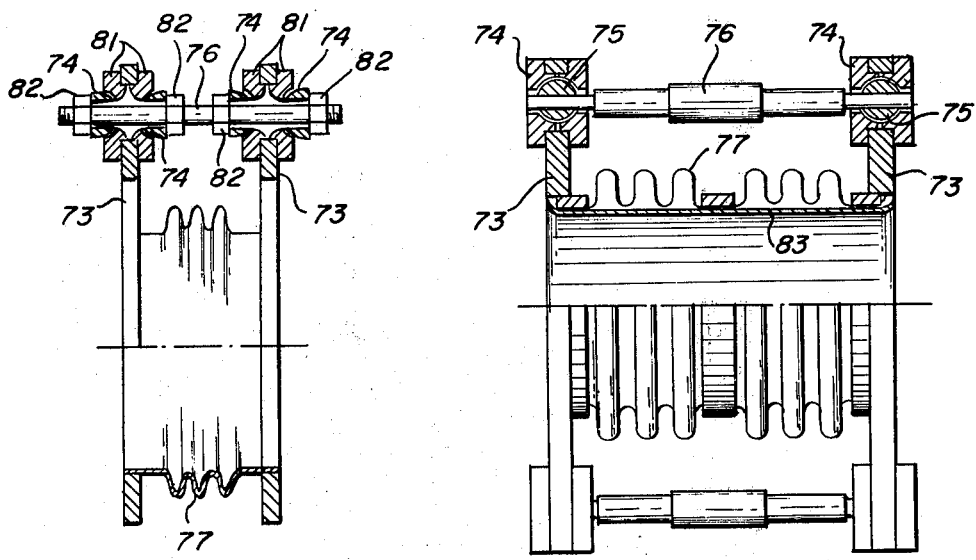
FIGS. 15 and 16 are side views with parts broken of second and third embodiments, respectively, of a coupling device in accord with the present invention.

Expansion Coupling, FIGS. 14 through 16

Next referring to FIGS. 14, 15 and 16, some preferred embodiments of an expansion coupling in accord with the present invention will be described.

In a first embodiment shown in FIG. 14, each of the front, intermediate and rear flanges 73 has two female connection members with a spherical seat 74 attached thereto and angularly spaced apart from each other by 180°. Ball or male members 75 slidably fitted into the spherical seats 74 of the front, intermediate and rear female members are interconnected with each other by a connecting rod 76 with threaded front and rear end portions screwed into the ball members 75. The connecting rods 76 between the front and intermediate flanges 73 are angularly displaced by 180° with respect to the connecting rods 76 between the intermediate and rear flanges 73. Bellows 77 are interposed between the front and intermediate flanges 73 and between the intermediate and rear flanges 73, respectively. The surface of each ball member 75 may be spherical only at a portion in contact with the spherical seat 74.

The expansion coupling with the above construction may be displaced in all directions, has sufficient resistance against the axial thrust and is compact in size.

The intermediate flanges 73 are connected with bolts 80 with each other with guide bushes 78 made of an oilless metal interposed therebetween. The adjacent flanges 73 are interconnected with each other by two connecting rods 76 in such a way that a universal joint may be provided.

The front flange 73 of the expansion coupling is securely attached to the gate valve 6 or the rear casing 30 while the rear flange 73 is freely coupled to the lance sealing device described above. In order to limit the displacement of the expansion coupling due to the compressive or tensile force exerted thereto when the lance 4 is advanced forwardly or backwardly, the lance 4 is made into contact with the inner surfaces of the guide bushes 78 having an inner diameter slightly greater than the outer diameter of the lance 4. The provision of the guide bushes 78 is very important because they prevent the buckling of the expansion coupling when it is exerted with the axial compressive force.

In the second embodiment shown in FIG. 15, each female connection member attached to flange 74 is formed with coaxial semispherical seats 74 in the front and rear surfaces, and the connecting rod 76, which is externally threaded throughout its length in the second embodiment, are extended through the bores of mating semespherical male members 81 fitted into the semispherical seats 74 with nuts 82 threadably fitted over the connecting rod 76 and pressed against the flat surfaces of the semispherical male members 81. The dimensions of the connecting rod 76 are of course so selected as to have sufficient strength to withstand the axial thrusts exerted thereto. The flanges 73 of the expansion coupling are interconnected in this manner by two or three connecting rods 76 which are equiangularly spaced apart from each other. In order to permit the smooth displacement in all directions, the clearances between the connecting rod 76 and the bore of the semispherical male member 81 and between the semispherical seat 74 and the semispherical male member 81 fitted therein must be suitably selected.

The third embodiment shown in FIG. 16 is substantially similar in construction to the first embodiment shown in FIG. 14 except that the inside of the bellows 77 is lined with an asbestos cloth 83 so as to prevent the intrusion of dust or the like into the valley portions.

The expansion couplings in accord with the present invention have the following advantages;

I. They may absorb the displacement in all directions so that the safe and reliable operation of the furnace gas sampling device may be ensured.

II. They can withstand the extensively heavy axial thrust; that is, the tensile and compressive forces or repeated tensile and compressive forces. In addition they can be made compact in size so that the gas sampling device may be reduced in size accordingly.

III. Installation allowances or tolerances may be considerably relaxed so that the design, fabrication and installation of the furnace gas sampling device may be much facilitated.

As described above, the furnace gas sampling device in accord with the present invention consists of the gate valve, the lance sealing device, the expansion coupling and other parts all of which are considerably improved for better performance so that the maintenance may be much facilitated, considerably high savings in labor can be attained and the cost may be remarkably reduced.

What is claimed is:

1. A device for sampling gases from a furnace consisting of the provision of
    a. a lance adapted to be moved axially forwardly or backwardly along guide frames by hydraulic driving cylinders, and
    b. a gate valve provided with a swingable valve disk for sealing the furnace when said lance is retracted out of the furnace and a dust discharge mechanism for discharging dust and the like accumulated in a valve box out of the valve box.

2. A device for sampling gases from a furnace as set forth in claim 1 consisting of the provision of a lance sealing device consisting of
    a housing through which said lance is extended, formed gland packings and oilless metals fitted over said lance in said housing and axially spaced apart from each other so as to define a space surrounded by the inner surface of said housing, the outer surface of said lance and the axially spaced apart formed gland packings, and an amorphous heat-resisting material supply system for forcing amorphous heat-resisting material into said space and maintaining a predetermined pressure of the amorphous heat-resisting material charged into said space.

3. A device for sampling gases from a furnace as set forth in claim 1 consisting of the provision of an expansion coupling wherein at least a pair of axially spaced flanges with a bellows interposed therebetween are interconnected by a plurality of connecting rods equiangularly spaced apart from each other, each end of said connecting rods being terminated into an externally threaded screw portion treadaly engaged with a male having a spherical or partly spherical surface which is slidably fitted into a mating spherical or partly spherical seat formed in a female connecting member attached to the flange.

4. A device for sampling gases from a furnace as set forth in claim 2 consisting of the provision of an expansion coupling wherein at least a pair of axially spaced flanges with a bellows interposed therebetween are interconnected with each other by a plurality of connecting rods equiangularly spaced apart from each other, each end of said connecting rods being terminated into an externally threaded acrew portion threadaly engaged with a male member having a spherical or partly spherical surface which is slidably fitted into a mating spherical or partly spherical seat formed in a female connecting member attached to a the flange.

* * * * *

UNITED STATES PATENT AND TRADEMARK OFFICE
CERTIFICATE OF CORRECTION

PATENT NO. : 4,054,060
DATED : October 18, 1977
INVENTOR(S) : Masayuki Ueno; Fumiaki Sano, both of Yokohama, Japan It is certified that error appears in the above-identified patent and that said Letters Patent are hereby corrected as shown below:

Claim 3, column 12, line 40, change "treadaly" to --threadably--

Claim 3, column 12, line 40, change "a male" to --a male member--

Claim 4, column 12, line 52, change "acrew" to --screw--

Claim 4, column 12, lines 52 and 53, change "threadaly" to --threadably--

Claim 4, column 12, line 56, change "a the flange" to --the flange--

Signed and Sealed this

Thirteenth Day of February 1979

[SEAL]

Attest:

RUTH C. MASON
Attesting Officer

DONALD W. BANNER
Commissioner of Patents and Trademarks